US012569229B2

(12) United States Patent　　　　(10) Patent No.:　US 12,569,229 B2

Chen et al.　　　　　　　　　　　　(45) Date of Patent:　　Mar. 10, 2026

(54) CAPTURING TRUNCATED PROTEOFORMS IN EXHALED BREATH FOR DIAGNOSIS AND TREATMENT OF DISEASES

(71) Applicant: Zeteo Tech, Inc., Sykesville, MD (US)

(72) Inventors: Dapeng Chen, Sykesville, MD (US); Wayne A. Bryden, Sykesville, MD (US); Michael McLoughlin, Sykesville, MD (US)

(73) Assignee: Zeteo Tech, Inc., Sykesville, MD (US)

( * ) Notice:　Subject to any disclaimer, the term of this patent is extended or adjusted under 35 U.S.C. 154(b) by 702 days.

(21) Appl. No.: 17/827,708

(22) Filed:　May 29, 2022

(65)　　　　　Prior Publication Data

US 2022/0323045 A1　　Oct. 13, 2022

Related U.S. Application Data

(63) Continuation-in-part of application No. PCT/US2022/022964, filed on Mar. 31, 2022.

(Continued)

(51) Int. Cl.
　　*G01N 1/40*　　　　(2006.01)
　　*A61B 5/00*　　　　(2006.01)
　　　　　　　(Continued)

(52) U.S. Cl.
　　CPC ............ *A61B 10/00* (2013.01); *A61B 5/0836* (2013.01); *A61B 5/097* (2013.01); *A61B 5/7203* (2013.01);
　　　　　　　(Continued)

(58) Field of Classification Search
　　CPC ............. G01N 1/4044; G01N 33/6848; G01N 33/6851; G01N 33/6893; G01N 2800/12; G01N 2800/26
　　See application file for complete search history.

(56)　　　　　References Cited

U.S. PATENT DOCUMENTS 6,062,392 A　　5/2000　Birmingham et al.
6,267,016 B1　　7/2001　Call et al.
　　　　　　(Continued)

FOREIGN PATENT DOCUMENTS

EP　　　3336543　　　6/2018
EP　　　2823300　　　10/2019
　　　　　　(Continued)

OTHER PUBLICATIONS

International Search Report and Written Opinion for PCT/US2020/048035, issued by ISA/KIPO on Dec. 30, 2020.
　　　　　　(Continued)

*Primary Examiner* — Peter J Macchiarolo
*Assistant Examiner* — Rodney T Frank
(74) *Attorney, Agent, or Firm* — Paradice & Li LLP; Anand S. Chellappa

(57)　　　　　ABSTRACT

Methods and devices to capture and analyze aerosolized particles such as protein biomarkers and their truncated proteoforms characteristic of a disease, including a respiratory disease, in exhaled breath to enable rapid detection of diseases are disclosed. The disclosed methods and systems selectively capture aerosolized particles using a packed bed column. The captured particles are then eluted using one or more solvents and analyzed using devices including mass spectrometry.

17 Claims, 5 Drawing Sheets

Related U.S. Application Data

Figure 1A:
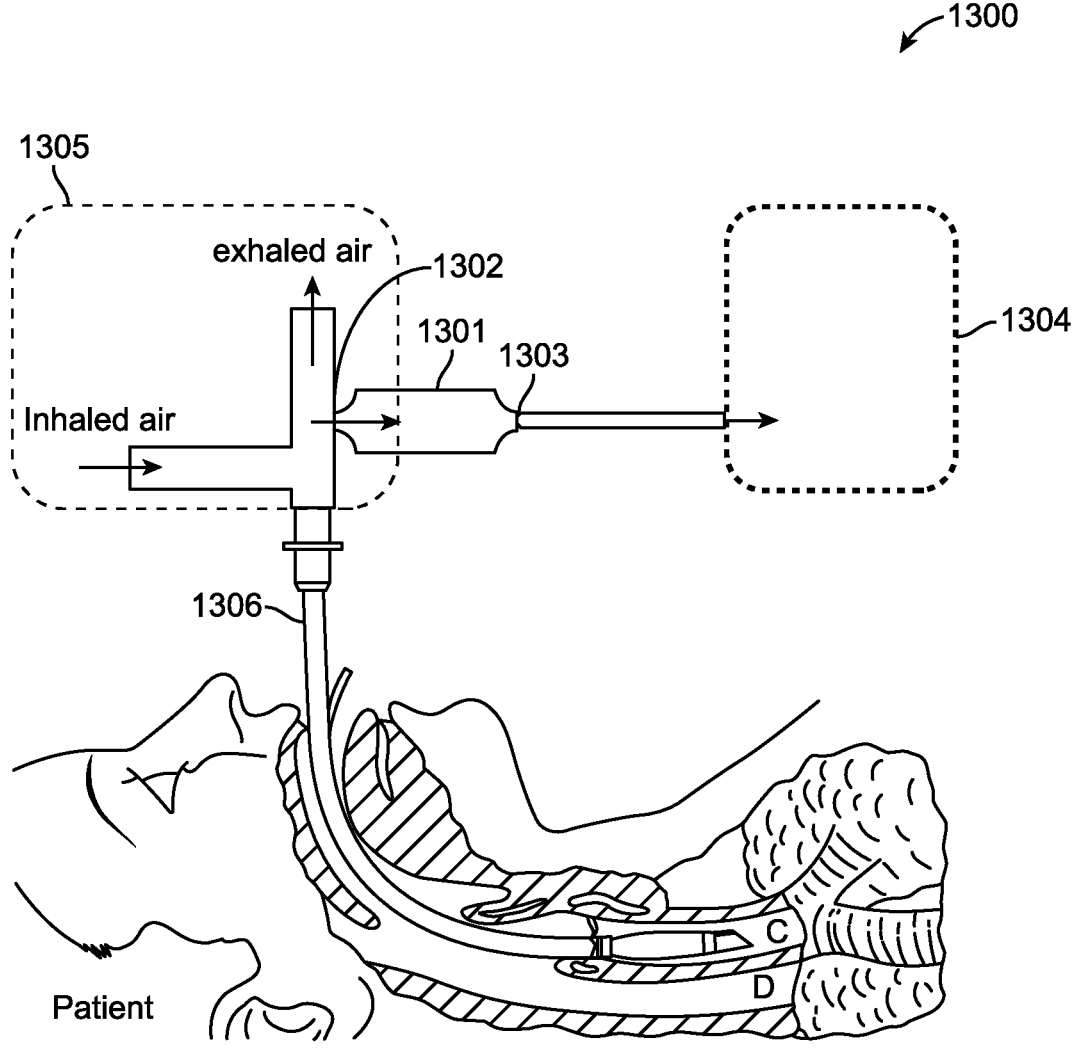

(60) Provisional application No. 63/325,435, filed on Mar. 30, 2022, provisional application No. 63/249,357, filed on Sep. 28, 2021, provisional application No. 63/169,130, filed on Mar. 31, 2021.

(51) Int. Cl.

| | |
|---|---|
| *A61B 5/083* | (2006.01) |
| *A61B 5/097* | (2006.01) |
| *A61B 10/00* | (2006.01) |
| *A61M 16/08* | (2006.01) |
| *G01N 33/68* | (2006.01) |
| *A61M 16/04* | (2006.01) |

(52) U.S. Cl.
CPC ...... *A61M 16/0808* (2013.01); *A61M 16/085* (2014.02); *G01N 1/4044* (2013.01); *G01N 33/6848* (2013.01); *G01N 33/6851* (2013.01); *G01N 33/6893* (2013.01); *A61B 2010/0087* (2013.01); *A61B 2560/0431* (2013.01); *A61M 16/04* (2013.01); *G01N 2800/12* (2013.01); *G01N 2800/26* (2013.01)

(56) References Cited

U.S. PATENT DOCUMENTS

| | | | |
|---|---|---|---|
| 7,364,553 B2 * | 4/2008 | Paz | A61B 5/0878 |
| | | | 600/529 |
| 7,779,840 B2 * | 8/2010 | Acker | A61M 16/0808 |
| | | | 128/205.12 |
| 8,409,870 B2 | 4/2013 | Van Wuijckhuijse et al. | |
| 8,424,523 B2 | 4/2013 | Ogilvie et al. | |
| 8,434,481 B2 | 5/2013 | Ogilvie et al. | |
| 8,434,483 B2 | 5/2013 | Patel et al. | |
| 8,944,059 B2 | 2/2015 | Mansour et al. | |
| 9,022,029 B2 | 5/2015 | Varga et al. | |
| 9,089,665 B2 | 7/2015 | Patel | |
| 9,675,773 B2 | 6/2017 | Colman et al. | |
| 10,632,276 B2 | 4/2020 | Fyfe et al. | |
| 10,926,052 B2 | 2/2021 | Colman et al. | |
| 11,135,392 B2 | 10/2021 | Oddo et al. | |
| 11,229,763 B2 | 1/2022 | Oddo et al. | |
| 11,246,506 B2 | 2/2022 | Gunneson et al. | |
| 11,359,733 B2 | 6/2022 | Oddo et al. | |
| 11,400,250 B2 | 8/2022 | Oddo et al. | |
| 11,547,322 B2 | 1/2023 | Lundin et al. | |
| 11,617,848 B2 | 4/2023 | Fyfe et al. | |
| 11,826,512 B2 | 11/2023 | Oddo et al. | |
| 11,896,366 B2 | 2/2024 | Cardin | |
| 12,091,056 B2 | 9/2024 | Ramakrishnan et al. | |
| 2003/0208132 A1 | 11/2003 | Baddour | |
| 2005/0137491 A1 | 6/2005 | Paz et al. | |
| 2007/0068811 A1 | 3/2007 | Tsukashima et al. | |
| 2008/0038207 A1 | 2/2008 | Edwards et al. | |
| 2009/0156952 A1 | 6/2009 | Hunter et al. | |
| 2012/0011918 A1 | 1/2012 | Bacal et al. | |
| 2012/0172679 A1 | 7/2012 | Logan et al. | |
| 2013/0217029 A1 | 8/2013 | Sislian et al. | |
| 2013/0327122 A1 | 12/2013 | Dutta et al. | |
| 2015/0377868 A1 | 12/2015 | Cooper et al. | |
| 2016/0020080 A1 | 1/2016 | Pyun et al. | |
| 2016/0022946 A1 | 1/2016 | Sislian et al. | |
| 2016/0231333 A1 | 8/2016 | Sutherland | |
| 2017/0035326 A1 | 2/2017 | King-Smith | |
| 2017/0119280 A1 | 5/2017 | Ahmad | |
| 2017/0299477 A1 | 10/2017 | Milton et al. | |
| 2017/0303822 A1 | 10/2017 | Allsworth et al. | |
| 2018/0246120 A1 | 8/2018 | Bryden et al. | |
| 2019/0000351 A1 | 1/2019 | Scampoli | |
| 2019/0094195 A1 | 3/2019 | Genter | |
| 2019/0282124 A1 | 9/2019 | Wu et al. | |
| 2020/0041485 A1 | 2/2020 | Funch-Nielsen | |
| 2020/0147333 A1 | 5/2020 | Stoll et al. | |
| 2020/0345266 A1 | 11/2020 | Schleich | |

| | | | |
|---|---|---|---|
| 2021/0318208 A1 | 10/2021 | Bayer et al. | |
| 2021/0321903 A1 | 10/2021 | Daniels | |
| 2021/0345956 A1 | 11/2021 | Keays et al. | |
| 2021/0386959 A1 | 12/2021 | Oddo et al. | |
| 2022/0034854 A1 | 2/2022 | Chen et al. | |
| 2022/0076783 A1 | 3/2022 | Cristescu et al. | |
| 2022/0183587 A1 | 6/2022 | Karshmer | |
| 2022/0322963 A1 * | 10/2022 | Bryden | A61B 5/097 |
| 2022/0323045 A1 * | 10/2022 | Chen | A61B 5/082 |
| 2022/0370751 A1 | 11/2022 | Oddo et al. | |
| 2022/0381766 A1 | 12/2022 | Cardin | |
| 2023/0157573 A1 | 5/2023 | Chen et al. | |
| 2023/0172484 A1 | 6/2023 | Lundin et al. | |
| 2023/0256189 A1 | 8/2023 | Fyfe et al. | |
| 2024/0197202 A1 | 6/2024 | Andrasko et al. | |
| 2024/0423497 A1 | 12/2024 | Höjer | |

FOREIGN PATENT DOCUMENTS

| | | |
|---|---|---|
| JP | H0989863 A | 4/1997 |
| JP | H09126958 | 5/1997 |
| JP | H10227725 A | 8/1998 |
| JP | 2006329779 A | 12/2006 |
| JP | 2011102747 A | 5/2011 |
| JP | 5848608 B2 | 1/2016 |
| JP | 2018194463 A | 12/2018 |
| JP | 2019184288 A | 10/2019 |
| JP | 2020534511 A | 11/2020 |
| KR | 1020160130229 | 11/2016 |
| WO | WO2004090534 A1 | 10/2004 |
| WO | WO2006012205 A2 | 2/2006 |
| WO | WO2009045163 A1 | 4/2009 |
| WO | WO2017197386 A1 | 11/2017 |
| WO | 2019011750 | 1/2019 |
| WO | WO2019145678 A1 | 8/2019 |
| WO | WO2021061330 A1 | 4/2021 |
| WO | WO2021201905 A1 | 10/2021 |

OTHER PUBLICATIONS

Written Opinion of ISA/KIPO for PCT/US2020/048040 issued Dec. 9, 2020.

J. Brennan McNeil, Ciara M. Shaver, V. Eric Kerchberger, Derek W. Russell, Brandon S. Grove, Melissa A. Warren, Nancy E. Wickersham, Lorraine B. Ware, W. Hayes McDonald, and Julie A. Bastarache, "Novel Method for Noninvasive Sampling of the Distal Airspace in Acute Respiratory Distress Syndrome," American J. Respiratory and Critical Care Medicine 197(8), Apr. 15, 2018.

Joerg Reifart, Christoph Liebetrau, Christian Troidl, Katharina Madlener and Andreas Rolf, "Noninvasive sampling of the distal airspace via HME-flter fuid is not useful to detect SARS-CoV-2 in intubated patients," Crit. Care (2021) 25:126.

B. Bake, P. Larsson, G. Ljungkvist, E. Ljungström, and A-C Olin, "Exhaled particles and small airways," Respiratory Research (2019) 20:8.

Fennelly K.P., Martyny J.W., Fulton K.E., Orme I.M., Cave D.M., et al. (2004) Cough-generated aerosols of *Mycobacterium tuberculosis*: a new method to study infectiousness. Am J Respir Crit Care Med 169: 604-609.

Dina Hashoul and Hossam Haick, "Sensors for detecting pulmonary diseases from exhaled breath," Eur. Respir. Rev. 2019; 28: 190011.

Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.

James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. Jan. 1, 2013; 47(4): 444-451.

Wood R., Morrow C., Barry C.E., III, Bryden W.A., Call C.J., Hickey A.J., et al.: Real-Time Investigation of Tuberculosis Transmission: Developing the Respiratory Aerosol Sampling Chamber (Rasc). PLoS One. 2016; 11(1): e0146658.

Rachel C. Wood, Angelique K. Luabeya, Kris M. Weigel, Alicia K. Wilbur, Lisa Jones-Engel, Mark Hatherill, and Gerard A. Cangelosi,

(56) References Cited

OTHER PUBLICATIONS

"Detection of *Mycobacterium tuberculosis* DNA on the oral mucosa of tuberculosis patients," Sci. Rep. 5, 8668 (2015).

Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

International Search Report of ISA/KIPO for PCT/US2020/048040 issued Dec. 9, 2020.

Chen et al., "A Novel System for the Comprehensive Collection of Nonvolatile Molecules from Human Exhaled Breath," Journal of Breath Research, vol. 15, No. 1, Oct. 20, 2020 (Oct. 20, 2020), p. 016001, XP09328706.

Sang Hoon Song et al., "Proteomic Profiling of Serum from Patients with Tuberculosis", Ann Lab Med 2014, 34(5), pp. 345-353, [retrieved on Jan. 18, 2025]. Retrieved from <URL: https://doi.org/10.3343/alm.2014.34.5.345>, pp. 347 and table 1.

International Search Report and Written Opinion of ISA/KIPO for PCT/US2024/052658 dated Feb. 6, 2025.

International Search Report and Written Opinion of ISA/KIPO for PCT/US2022/022964 dated Jul. 13, 2022.

International Preliminary Report on Patentability (with Annex) for PCT/US2022/022964 dated May 11, 2023 by IPEA/KR.

International Search Report and Written Opinion of ISA/KIPO for PCT/US2023/029760 dated Nov. 24, 2023.

International Search Report for PCT/US2020/048035, issued by ISA/KIPO on Dec. 30, 2020.

N. Ahmed, R. Babaei-Jadidi, S. K. Howell, P. J. Beisswenger & P. J. Thornalley, "Degradation products of proteins damaged by glycation, oxidation and nitration in clinical type 1 diabetes," Diabetologia 48, 1590-1603 (2005).

Dapeng Chen, Lucia Geis-Asteggiante, Fabio P. Gomes, Suzanne Ostrand-Rosenberg, and Catherine Fenselau, "Top-Down Proteomic Characterization of Truncated Proteoforms," J. Proteome Res. 2019, 18, 11, 4013-4019.

Allan Lipton, Kim Leitzel, Suhail M. Ali, Hyma V. Polimera, Vinod Nagabhairu, Eric Marks, Angelique E. Richardson, Laura Krecko, Ayesha Ali, Wolfgang Koestler, Francisco J. Esteva, Diana J. Leeming, Morten A. Karsdal, Nicholas Willumsen, "High turnover of extracellular matrix reflected by specific protein fragments measured in serum is associated with poor outcomes in two metastatic breast cancer cohorts," Intl. J. Cancer, 2018, 43 (11), 3027-3034.

Piero Parchi, Shu G. Chen, Paul Brown, Wenquan Zou, Sabina Capellari, Herbert Budka, Johannes Hainfellner, Patricio F. Reyes, Gregory T. Golden, Jean J. Hauw, D. Carleton Gajdusek, and Pierluigi Gambetti, "Different patterns of truncated prion protein fragments correlate with distinct phenotypes in P102L Gerstmann-Sträussler-Scheinker disease," Neuroscience, 95 (14), 8322-8327 (1998).

Helen Tsai, Brett S. Phinney, Gabriela Grigorean, Michelle R. Salemi, Hooman H. Rashidi, John Pepper, and Nam K. Tran, "Identification of Endogenous Peptides in Nasal Swab Transport Media used in MALDI-TOF-MS Based COVID-19 Screening," ACS Omega 2022, 7, 20, 17462-17471.

Hunt, J., "Exhaled breath condensate: An evolving tool for noninvasive evaluation of lung disease," J. Allergy Clin. Immunol. 2002; 110:28-34.

Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.

Guise M T et al: "An experimental investigation of aerosol collection utilizing packed beds of silica aerogel microspheres", Journal of Non-Crystalline Solids, North-Holland Physics Publishing. Amsterdam, NL, vol. 285, No. 1-3, Jun. 1, 2001 (Jun. 1, 2001), pp. 317-322, XP004242941, ISSN: 0022-3093, DOI: 10.1016/S0022-3093(01)00473-2. (Year: 2001).

International Preliminary Report on Patentability (with Annex) for PCT/US2023/029760 dated Oct. 8, 2024 by IPEA/KR.

"Ventilator/Ventilator Support, What to Expect," NIH, National Heart, Lung, and Blood Institute, downloaded from the internet on Jul. 8, 2024 at <https://www.nhlbi.nih.gov/health/ventilator/what-to-expect#:~:text=Ventilators>, 7-pages, last updated Mar. 24, 2022.

International Preliminary Report on Patentability (with Annex) for PCT/US2020/048035, mailed Mar. 22, 2022 by IPEA/KR.

Bardet, C. et al. (Jan. 23, 2021) Early and specific targeted mass spectrometry-based identification of bacteria in endotracheal aspirates of patients suspected with ventilator-associated pneumonia. European Journal of Clinical Microbiology & Infectious diseases. vol. 40, p. 1291-1301. (Year: 2021).

MaxiQuant technical note (2010): MultiQuant Software 2.0 for targeted protein/ peptide quantification,# 0921210-02. (Year: 2010).

Lopez-Sanchez, L. et al. (2017) Exhaled breath condensate biomarkers for the early diagnosis of lung cancer using proteomics. American Journal of Physiological Lung Cell Molecular Physiology, vol. 313, L664-L676. (Year: 2017).

Qu, J. et al. (2010) Proteomic expression profiling of Haemophilus influenzae grown in pooled human sputum from adults with chronic obstructive pulmonary disease reveal antioxidant and stress response. BMC Microbiology, vol. 10: 162, 12 pages. (Year: 2010).

Dupree (2020) A critical review of Bottom-up proteomics: the good, the bad and the future of this field. Proteomes, vol. 8 No. 14, 8030114, 26 pages. (Year: 2020).

Amann, A et al. (2014) Analysis of exhaled breath for disease detection. Ann Rev Anal Chem. vol. 7:435-482. (Year: 2014).

Bregy (2018) Real-time mass spectrometric identification of metabolites characteristic of chronic obstructive pulmonary disease in exhaled breath. Clinical Mass Spectrometry, vol. 7, 29-35. (Year: 2018).

Ross, M.H, et al (2019) Host-based diagnostics for acute respiratory infections. Clinical Therapeutics, vol. 41, No. 10, p. 1923-1938. (Year: 2019).

"Hsueh, M-F. (2016) Elucidating the molecular composition of cartilage by proteomics. Journal of Proteome Research, vol. 15, p. 374-388. (Year: 2016)".

Stegemann, C. (2013) Proteomic identification of matrix metalloproteinase substrates in the human vasculature. Circ Cardiovasc Genet. vol. 6, p. 106-117 (Year: 2013).

\* cited by examiner

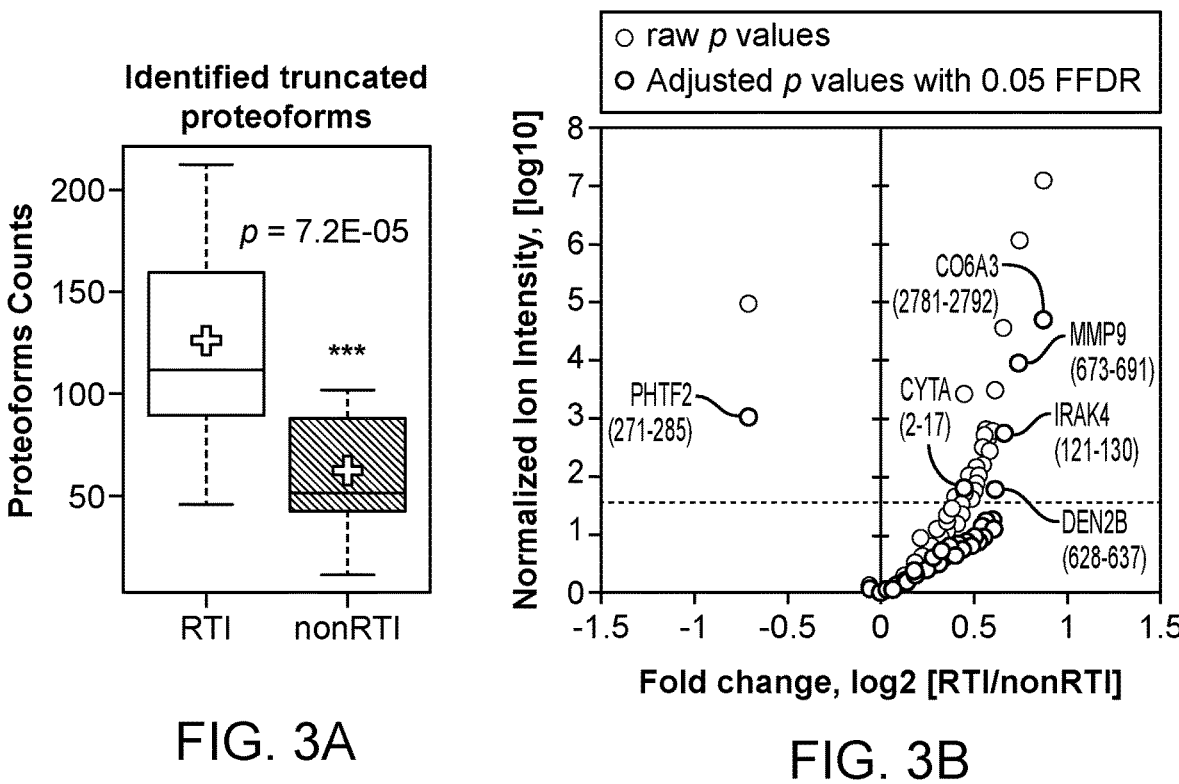
FIG. 3A
FIG. 3B
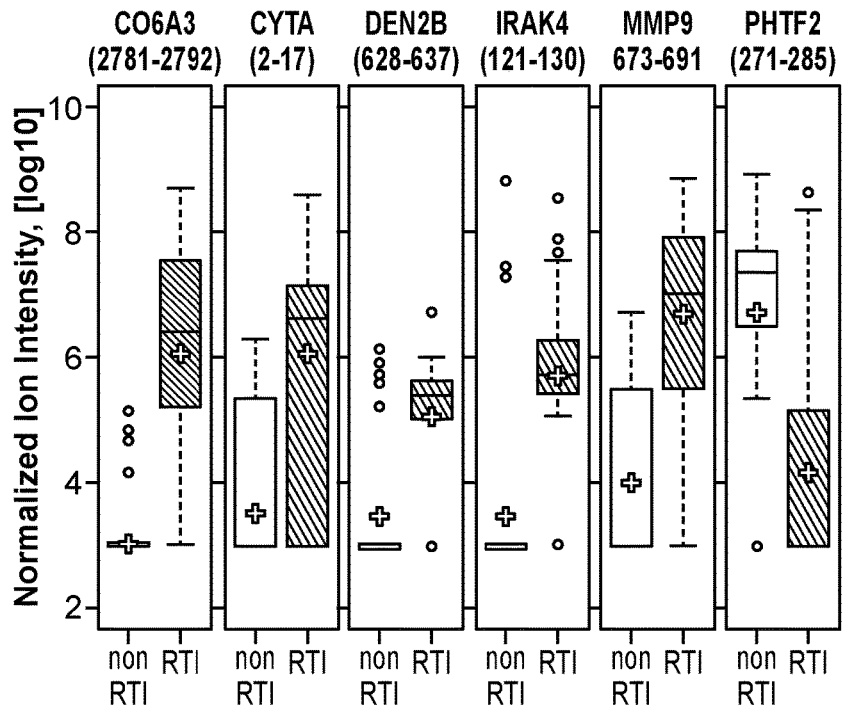
FIG. 3C

| CO6A3 (2781-2792) | CYTA (2-17) | DEN2B (628-637) | IRAK4 (121-130) | MMP9 673-691 | PHTF2 (271-285) |
|---|---|---|---|---|---|
| AUC: 88.5% | AUC: 79.1% | AUC: 52.2% | AUC: 52.0% | AUC: 79.3% | AUC: 60.5% |

Multiple Logistic Regression with All 6 Proteoforms

AUC: 95.7%

CAPTURING TRUNCATED PROTEOFORMS IN EXHALED BREATH FOR DIAGNOSIS AND TREATMENT OF DISEASES

RELATED APPLICATIONS

This application is a continuation-in-part of International Application No. PCT/US22/22964, filed Mar. 31, 2022, which is related to and claims the benefit of U.S. Provisional Appl. No. 63/169,130, filed Mar. 31, 2021, and titled "Diagnosis of Respiratory Diseases By Capturing Aerosolized Biomaterial Particles Using Packed Bed Systems and Methods," U.S. Provisional Appl. No. 63/249,357, filed Sep. 28, 2021 and titled "Diagnosis of Respiratory Diseases By Capturing Aerosolized Biomaterial Particles Using Packed Bed Systems and Methods," and U.S. Provisional Appl. No. 63/325,435, filed Mar. 30, 2022, and titled "Diagnosis of Respiratory Diseases By Capturing Aerosolized Biomaterial Particles Using Packed Bed Systems and Methods," the entire disclosures of which are incorporated herein by reference.

FEDERALLY SPONSORED RESEARCH AND DEVELOPMENT

None.

FIELD

This disclosure relates to methods and devices for capturing and analyzing aerosolized organic biomaterials such as virus and bacteria particles and related truncated proteoforms in exhaled breath using packed bed columns to enable rapid, low-cost detection of several diseases including respiratory tract diseases such as COVID-19. More particularly, but not by way of limitation, the present disclosure relates to methods and devices for analyzing truncated proteoforms and non volatile organic particles in exhaled breath to detect diseases using mass spectrometry.

BACKGROUND

Exhaled breath aerosols contain non-volatile organic bio-markers produced by human biological processes, including metabolic, immunological, and inflammatory processes, and the composition of these compounds and proteoforms may be viewed as indicators for human health. The detection of these protein biomarkers and their truncated proteoforms using analysis of exhaled breath could be used to monitor, screen, diagnose, and distinguish between healthy persons and persons with health issues such as obesity, diabetes, liver cancer, lung cancer, and the like. The capture of these biomarkers from exhaled breath and subsequent analysis could reveal health risk factors and assist with diagnosis, treatment and mitigating the spread of diseases.

Although research has shown that respiratory diseases can be detected from breath aerosol and breath condensate, modern clinical tests for infections or diseases such as COVID-19, tuberculosis, influenza, pneumonia continue to utilize sputum, blood, or nasal swabs. Coronavirus Disease (COVID-19) is a disease caused by the newly emerged coronavirus SARS-CoV-2. This new coronavirus is a respiratory virus and spreads primarily through droplets generated when an infected person coughs or sneezes, or through droplets of saliva or discharge from the nose. The novel coronavirus is highly contagious and has created a pandemic. Further, tuberculosis (TB) has surpassed HIV/AIDS as a global killer with more than 4000 daily deaths. (Patterson, B., et al., 2018). In communities with highly prevalent HIV, *Mycobacterium tuberculosis* (Mtb) genotyping studies have found that recent transmission, rather than reactivation, accounts for the majority (54%) of incident TB cases. The physical process of TB transmission remains poorly understood and the application of new technologies to elucidate key events in infectious aerosol production, release, and inhalation, has been slow. Interruption of transmission would likely have a rapid, measurable impact on TB incidence. To mitigate transmission of respiratory diseases, rapid disease detection tools are needed.

The time associated with a diagnostic assay is a critical parameter for a fielded, or "point of care" test. Active Case Finding ("ACF") is an example of a fielded diagnostic assay because, by definition, ACF takes place outside the healthcare system. According to the World Health Organization, ACF is a "systematic identification of people with suspected active TB, using tests, examinations, or other procedures that can applied rapidly." In the U.S., a point-of-care test needs to provide an answer in preferably 20 minutes or less. The GeneXpert assay (Cepheid, Inc., Sunnyvale, CA) may be used to provide diagnosis in about one hour. The GeneXpert genetic assay is based on polymerase chain reaction (PCR) and may be used to analyze a sample for respiratory disease diagnosis. This assay is expensive to implement on a "cost per test" basis, and therefore it is not yet widely deployed. Because of high cost, it is not used to screen patients who appear healthy (non-symptomatic) but might have TB infection in developing countries, but rather, is used to confirm a diagnosis that is strongly suspected based on other tests or factors. The goal of ACF is to get those infected to treatment earlier, thereby reducing the average period of infection and the spread of the disease. In the case of TB, by the time an individual goes to a clinic for help, that person may have transmitted the infection to between about 10 other people and about 115 other people. ACF can help to reduce or prevent significant TB transmission. The diagnostic systems and methods such as sputum analysis and blood analysis are either not automated and autonomously operated, or not rapid. Many have expensive assays with reagents that are consumed for each analysis, and thus, do not have general utility for active case finding, particularly in developing and under-developed countries.

There is increasing interest in new diagnostic tools for diseases, including respiratory diseases, using exhaled breath. Exhaled breath contains aerosols ("EBA") and vapors can be collected noninvasively and analyzed for characteristics to elucidate physiologic and pathologic processes in the lung. (Hunt, 2002). EBA analysis appears to be a compelling diagnostic tool for TB detection that provides for rapid analysis, portability, and low cost because the need for expensive assays and consumables are eliminated. To capture breath for assay, exhaled air is passed through a condensing apparatus to produce an accumulation of fluid that is referred to as exhaled breath condensate ("EBC"). Although predominantly derived from water vapor, EBC has dissolved within it nonvolatile compounds, including cytokines, lipids, surfactant, ions, oxidation products, adenosine, histamine, acetylcholine, and serotonin. In addition, EBC traps potentially volatile water-soluble compounds, including ammonia, hydrogen peroxide, and ethanol, and other volatile organic compounds. EBC has readily measurable pH. EBC contains aerosolized airway lining fluid and volatile compounds that provide noninvasive indications of ongoing biochemical and inflammatory activities in the lung. Rapid increase in interest in EBC has resulted from the recognition that in lung disease, EBC has measurable characteristics that can be used to differentiate between infected and healthy individuals. These assays have provided evidence of airway and lung redox deviation, acid-base status, and the degree and type of inflammation in acute and chronic asthma, chronic obstructive pulmonary disease, adult respiratory distress syndrome, occupational diseases, and cystic fibrosis. Characterized by uncertain and variable degrees of dilution, EBC may not provide precise assessment of individual solute concentrations within the native airway lining fluid. However, it can provide useful information when concentrations differ substantially between health and disease or are based on ratios of solutes found in the sample.

Patterson et al. (2018) used a respiratory aerosol sampling chamber (RASC), a novel apparatus designed to optimize patient-derived exhaled breath aerosol sampling, and to isolate and accumulate respirable aerosol from a single patient. Environmental sampling detects the Mtb present after a period of ageing in the chamber air. 35 newly diagnosed, GeneXpert sputum-positive, TB patients were monitored during one-hour confinement in the RASC chamber which has a volume of about 1.4 m$^3$. The GeneXpert PCR assay for TB can accept a sputum sample and provide a positive or negative result in about one hour. The chamber incorporated aerodynamic particle size detection, viable and non-viable sampling devices, real-time $CO_2$ monitoring, and cough sound-recording. Microbiological culture and droplet digital polymerase chain reaction (ddPCR) were used to detect Mtb in each of the bio-aerosol collection devices. Mtb was detected in 77% of aerosol samples and 42% of samples were positive by mycobacterial culture and 92% were positive by ddPCR. A correlation was found between cough rate and culturable bioaerosol. Mtb was detected on all viable cascade impactor stages with a peak at aerosol sizes 2.0-3.5 me. This suggests a median of 0.09 CFU/litre of exhaled air for the aerosol culture positives and an estimated median concentration of $4.5 \times 10^7$ CFU/ml of exhaled particulate bio-aerosol. Mtb was detected in bioaerosols exhaled by a majority of the untreated TB-patients using the RASC chamber. Molecular detection was found to be more sensitive that Mtb culture on solid media. Exhaled breath analytical tools have not been commercialized for ACF because methods and devices to efficiently collect and concentrate the trace amounts of analyte present in exhaled breath are lacking. Furthermore, there is no standard or methodology to assess how much exhaled breath is sufficient for a particular diagnosis.

The disclosed exemplary devices and methods overcome these limitations by collecting exhaled breath aerosol and breath condensate at high flow rate, high efficiency, and into relatively concentrated samples. Further, size sorting of aerosol can be incorporated to increase the signal to noise ratio for specific analytes prior to collection of the analytes. The concentrated samples may then be analyzed by several methods, but preferably, using methods that are sensitive, rapid, and highly specific to the analytes of interest. More preferably, the analysis will be rapid, and near real-time. Mass spectrometry, real-time PCR, and immunoassays have the highest potential to be sensitive, specific and nearly real-time. Sample collection methods are needed that can be coupled with fast diagnostic tools such as mass spectrometry ("MS") that is more rapid and reliable than sputum analysis and less invasive than blood analysis to provide a diagnostic assay that is fast, sensitive, specific and preferably, characterized by low cost per test. Such a system could be used for active case finding (ACF) of respiratory tract diseases and also to monitor the status of patients who use ventilators to assist breathing in a hospital intensive care unit. To be effective, the sample collection and diagnostic system must be rapid and inexpensive on a "per diagnosis" basis. Low cost-per-test is a requirement for screening a large number of individuals to proactively prevent disease transmission to search for the few that are indeed infected. Low-cost devices and methods would also be required for point-of-care diagnosis of influenza and other pathogenic viruses because patients probably infected with a "common cold" may be infected with rhinovirus. In some cases, the respiratory infection will be driven by a bacterial or fungal microbe and may be treatable with antibiotics. In other cases, the microbe may be resistant to antibiotics, and a diagnostic method that can identify microbial resistance to antibiotics is preferable. Rapid EBA methods for distinguishing between viral and bacterial infections in the respiratory tract are desired while minimizing the occurrence of false negatives due to an insufficient sample volume. Mass spectrometry, genomics methods including PCR, and immunoassays have the highest potential to be sensitive and specific. Mass spectrometry, and in particular, MALDI time-of-flight mass spectrometry (MALDI-TOFMS), is a preferred diagnostic tool for analysis EBA and EBC samples because it has been demonstrated to be sensitive, specific and near real-time.

BRIEF DISCLOSURE

Disclosed in an exemplary exhaled breath collection system to capture truncated proteoforms in exhaled breath for diagnosis and treatment of diseases, comprising one or more sample capture elements comprising a packed bed column in each to selectively capture aerosolized truncated proteoforms in the exhaled breath produced by a patient, and, a subsystem comprising at least one of a pump, a power supply, and a controller wherein the subsystem is disposed in fluid communication with the sample capture element and is configured to control the operation of the sample capture element and wherein the pump is configured to draw the exhaled air aerosol into the sample capture element. The subsystem may further comprise at least one of a $CO_2$ sensor and a particle counter disposed between the sample capture element and the pump. The subsystem may be disposed in a portable enclosure. The subsystem may further comprise a trap disposed between the sample capture element and the pump and configured to trap exhaled breath condensate (EBC) comprising at least one of water vapor, volatile organic components, and non-volatile organic components that pass through the packed bed. The packed bed column may comprise solid particles comprising at least one of resins, cellulose, silica, agarose, and hydrated $Fe_3O_4$ nanoparticles. The packed bed column may comprise at least one of resin beads having C18 functional groups on the surface, cellulose beads having sulfate ester functional groups on the surface, and mixtures thereof. The resin beads and cellulose beads may have a nominal diameter of at least about 20 μm. The resin beads and cellulose beads may have a nominal diameter of between about 40 μm and about 150 μm. The beads may be packed between two porous polymeric frit discs. The nominal flow rate drawn through the bed using the pump may be between about 200 ml/min and about 3 L/min. The subsystem may be configured to be fluidly and electrically coupled to the sample capture element using quick connect/disconnect couplings configured to detect proper mechanical and electrical contact and alert a user via a graphical user interface disposed on the subsystem and an audible alarm.

Disclosed is an exemplary system for diagnosis and treatment of diseases by capturing truncated proteoforms in exhaled breath, the system comprising the exhaled breath collection system as previously disclosed above, a sample extraction system to extract the captured truncated proteoforms characteristic of the diseases from the packed bed column into one or more liquid samples, and an analytical device to analyze the truncated proteoforms in the one more liquid samples. The extraction system may comprise means to flush the packed bed column with at least one solvent and to collect the solvent comprising truncated proteoforms from the packed bed. The at least one solvent may comprise at least one of acetonitrile, methanol, trifluoro acetic acid (TFA), isopropanol (IPA), the remaining being water. The one or more solvents may comprise between about 50 vol.-% and about 70 vol.-% acetonitrile in water, between about 50 vol.-% and about 70 vol.-% isopropanol in water, and between about 0.05 vol.-% TFA in water. The analytical device may comprise at least one of PCR, ELISA, rt-PCR, mass spectrometer (MS), MALDI-MS, ESI-MS, and MALDI-TOFMS, and LC-MS/MS.

Disclosed is an exemplary exhaled breath collection system to capture aerosol particles in exhaled breath for diagnosis and treatment of a patient infected with a respiratory disease and connected to a ventilator to assist the breathing of the infected patient, the system comprising. The system may comprise one or more sample capture elements comprising a packed bed column in each to selectively capture the aerosol particles in the exhaled breath produced by a patient wherein the sample capture element is removably connected to the exhaled air tubing of the ventilator, and a subsystem comprising at least one of a pump, a power supply, and a controller wherein the subsystem is disposed in fluid communication with the sample capture element and is configured to control the operation of the sample capture element and wherein the pump is configured to draw the exhaled air aerosol into the sample capture element. The aerosol particles in exhaled breath may comprise at least one of microbes, viruses, metabolite biomarkers, truncated proteoforms, and proteomic biomarkers characteristic of the respiratory disease.

Disclosed is an exemplary method for monitoring the status of a patient infected with a respiratory disease and connected to a ventilator to assist the breathing of the infected patient, the method comprising providing a sample collection system removably connected to the exhaled air tubing of the ventilator provided to assist the breathing of the infected patient, the system comprising one or more sample capture elements comprising a packed bed column in each to selectively capture aerosol particles in the exhaled air produced by the patient wherein the aerosol particles are characteristic of the respiratory disease, and a pump in fluid communication with the sample capture element and configured to draw the exhaled air aerosol into the sample capture element, extracting the captured aerosol particles from the packed bed column into one or more liquid samples, and analyzing the aerosol particles in the one or more liquid samples to determine the presence or absence of the respiratory disease. The exemplary method may further comprise the step of washing the column using at least one of 70% ACN, water, and 0.05% TFA prior to removably connecting the sample collection system to the exhaled air tubing of the ventilator. The extracting step may comprise flushing the packed bed column first with about 50 vol.-% ACN and subsequently with about 70 vol.-% IPA. The analyzing step may comprise analyzing the sample plate using at least one of PCR, ELISA, rt-PCR, mass spectrometer (MS), MALDI-MS, ESI-MS, and MALDI-TOFMS, and LC-MS/MS. The method may further comprise a sample processing step comprising mixing the one or more samples with a MALDI matrix and applying the one or more mixed samples and MALDI matrix to one or more sample plates. The method may further comprise a sample processing step comprising subjecting the one or more liquid samples extracted from the sample extraction system to protein digestion to generate a peptide sample characteristic of the respiratory disease. The sample processing step may further comprise mixing the peptide sample with a MALDI matrix and applying the mixed sample and MALDI matrix to a sample plate. The analyzing step may comprise analyzing the sample plate using at least one of PCR, ELISA, rt-PCR, mass spectrometer (MS), MALDI-MS, ESI-MS, and MALDI-TOFMS, and LC-MS/MS.

Disclosed is an exemplary method to confirm whether an intubated patient is diagnosed with a respiratory tract infection comprising providing a sample collection system removably connected to the exhaled air tubing of the ventilator provided to assist the breathing of the infected patient, the system comprising one or more sample capture elements comprising a packed bed column in each to selectively capture aerosol particles in the exhaled air produced by the patient wherein the aerosol particles are characteristic of the respiratory disease, and a subsystem comprising at least one of a pump, a power supply, and a controller wherein the subsystem is disposed in fluid communication with the sample capture element and is configured to control the operation of the sample capture element and wherein the pump is configured to draw the exhaled air aerosol into the sample capture element, extracting the captured organic compounds from the packed bed column into one or more liquid samples, analyzing the one or more liquid samples using mass spectrometry to obtain raw mass spectra and confirming whether the patient is infected with a respiratory tract infection if the mass spectra comprise a class of truncated proteoforms comprising protein CO6A3 (amino acid 2781-2792), CYTA (2-17), DEN2B (628-637), IRAK4 (121-130), MMP9 (673-691), and PHTF2 (271-285).

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

Figure 1B:
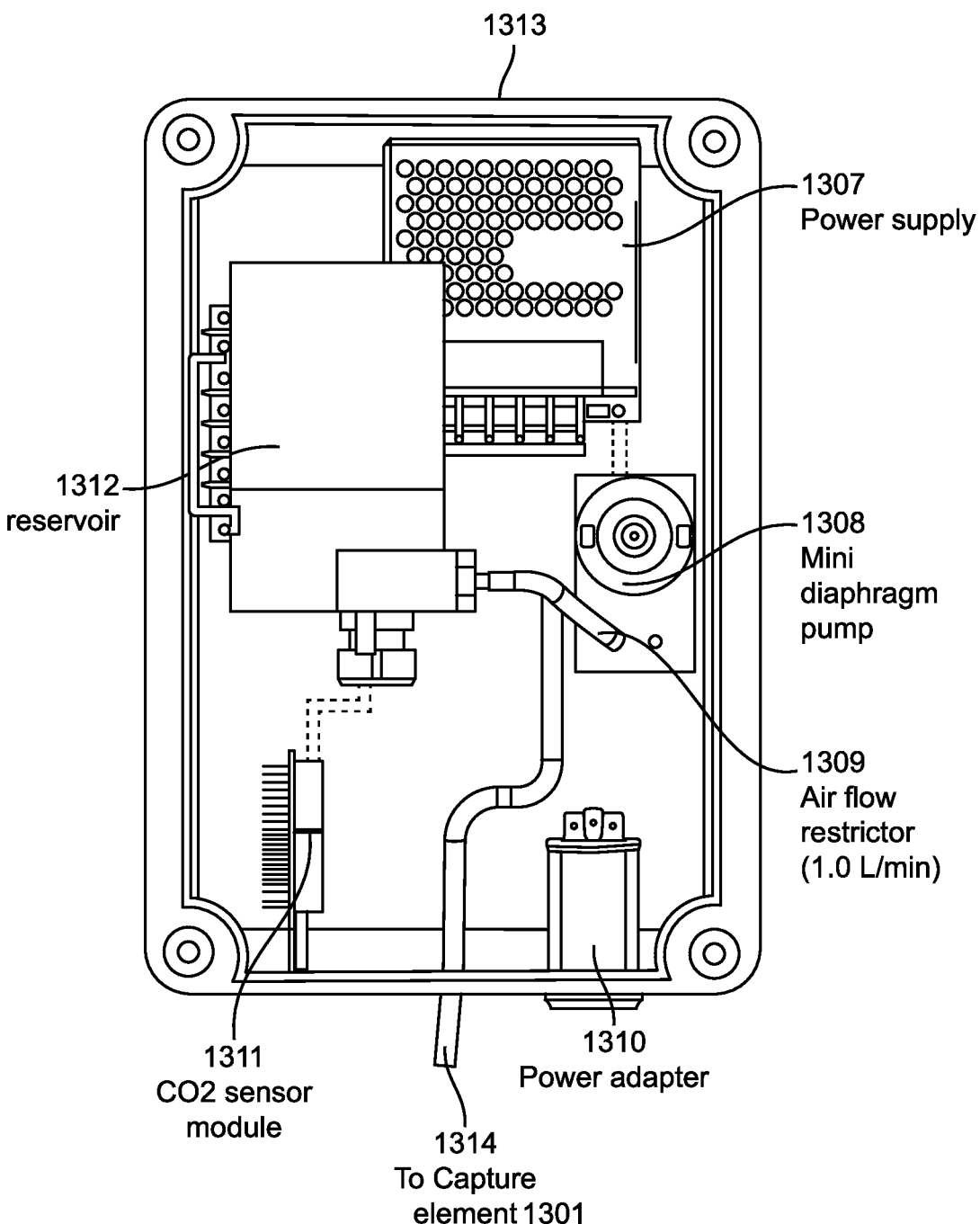

The foregoing aspects and many of the attendant advantages of this disclosure will become more readily appreciated as the same becomes better understood by reference to the following detailed description, when taken in conjunction with the accompanying drawings, wherein:

FIG. 1A-B. (A) Schematic diagram of an exemplary exhaled air aerosol collection system for use with a ventilator connected to patients diagnosed with COVID-19 in intensive care units and (B) schematic diagram of an exemplary portable accessory and control system configured to operate the aerosol collection system connected to a ventilator.

Figure 2:
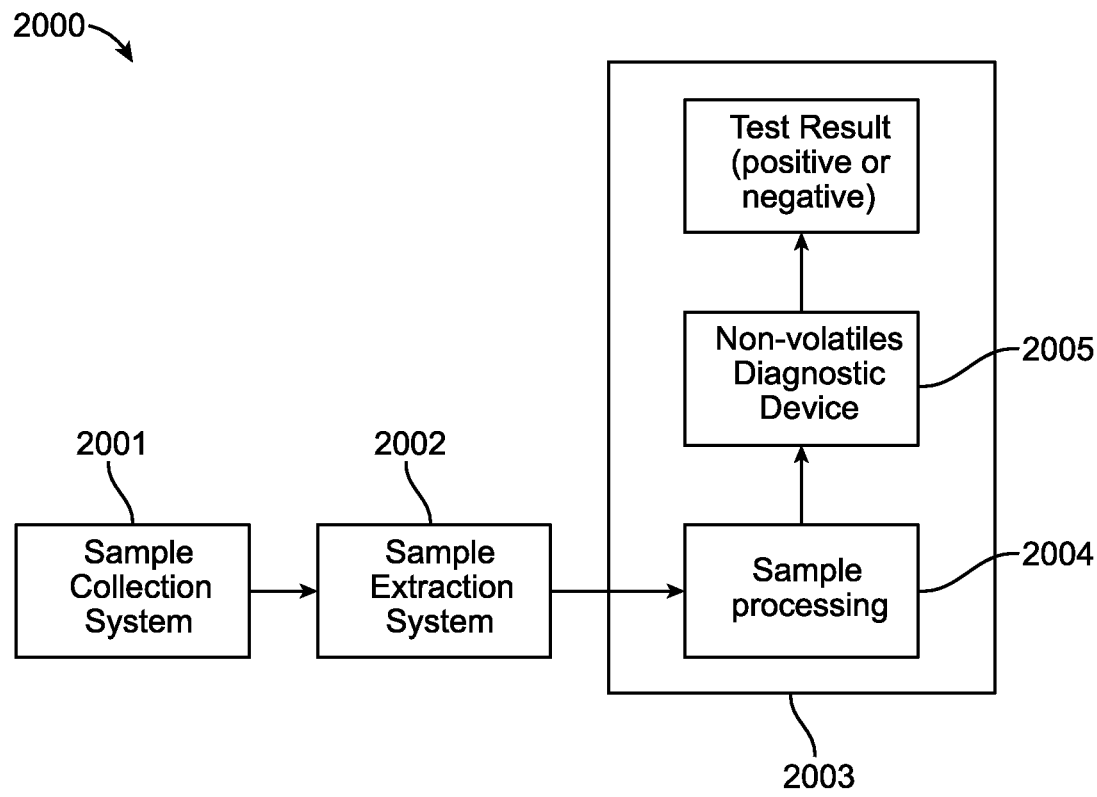

FIG. 2. Schematic diagram of an exemplary diagnostic system for respiratory diseases comprising an exemplary exhaled air sample collection system.

FIGS. 3A-E. Box and Whisker Plot for distinguishing between RTI patients and non-RTI patients using a class of 263 truncated proteoforms identified using mass spectrometry analysis of exhaled breath aerosols (A), volcano plot to distinguish between RTI patient and non-RTI patients based on the ion intensities of six truncated proteoforms (B), Box and Whisker Plot for distinguishing between RTI patients and non-RTI patients using a select class of 6 truncated proteoforms identified using mass spectrometry analysis of exhaled breath aerosols (C), ROC curves with AUC values for each of the 6 truncated proteoforms (D); ROC curve with AUC value for a general linear model using the select class of the 6 truncated proteoforms (E).

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this disclosure, aerosol generally means a suspension of particles dispersed in air or gas. "Autonomous" diagnostic systems and methods mean generating a diagnostic test result "with no or minimal intervention by a medical professional." The U.S. FDA classifies medical devices based on the risks associated with the device and by evaluating the amount of regulation that provides a reasonable assurance of the device's safety and effectiveness. Devices are classified into one of three regulatory classes: class I, class II, or class III. Class I includes devices with the lowest risk and Class III includes those with the greatest risk. All classes of devices as subject to General Controls. General Controls are the baseline requirements of the Food, Drug and Cosmetic (FD&C) Act that apply to all medical devices. In vitro diagnostic products are those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body. The exemplary devices disclosed herein can operate and produce a high-confidence result autonomously, and consequently, has the potential to be regulated as a Class I device. In some regions of the world with high burdens of TB infection, access to medically trained personnel is very limited. An autonomous diagnostic system is preferred to one that is not autonomous.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified." Unless otherwise specified, the concentration of chemicals, solvents and the like disclosed as a percentage refer to vol.-%.

DETAILED DISCLOSURE

Breath aerosol particles contain a variety of nonvolatile organic biomolecules such as metabolites, lipids, and proteins. The aerosol particles in exhaled breath may comprises at least one of microbes, viruses, metabolite biomarkers, lipid biomarkers, and proteomic biomarkers, for example, truncated proteoforms, which are characteristic of respiratory diseases and other diseases. Further, these nonvolatile molecules have a wide particle size distribution ranging from a sub-micron size to about 10 microns in size. Breath collection and disease diagnostic systems and methods that can efficiently capture different types of nonvolatile molecules of different particle sizes from exhaled breath are required. Particular aspects of the invention are described below in considerable detail for the purpose for illustrating the compositions, and principles, and operations of the disclosed methods and systems. However, various modifications may be made, and the scope of the invention is not limited to the exemplary aspects described.

Disclosed is an exemplary system 1300 (FIG. 1A) and method for capturing exhaled air aerosols by disposing exemplary sample capture element 1301 comprising a packed bed column in fluid communication with ventilator 1305. Ventilator 1305 is a life support machine and is used in intensive care units for patients who cannot breathe on their own. For example, patients with severe symptoms of COVID-19 may need the assistance of a ventilator to breathe. A tube 1306 is inserted through the patient's mouth or nose directly into the trachea. The ventilator pushes air into the lungs through this tube and forces the person to inhale. The ventilator typically forces air in for one second, pauses for about three seconds to allow the patient to exhale through the same tube, and then repeats the cycle. Inlet end 1302 of capture element 1301 is removably connected and preferably directly to the exhaled air tubing of the ventilator to minimize particle loss. Outlet end 1303 may be removably connected to pump 1308 in subsystem 1304 (details shown in subsystem 1313) using a tubing to draw in exhaled air through the packed bed column in element 1301 at a flow rate of between about 200 ml/min and about 2.5 L/min. System 1300 may comprise a trap disposed between end 1303 and subsystem 1313 to collect any condensate. The trap may be cooled to a temperature below ambient temperature. An optional HEPA filter and a needle valve or flow meter may be installed between the trap and the pump. $CO_2$ in exhaled breath passes through the packed bed column. To determine if exhaled breath sample volume is adequate, a $CO_2$ sensor may be disposed between the outlet end 1303 and the trap. $CO_2$ monitoring allows for an approximation of the exhaled air volume. A particle counter may also be installed upstream of capture element 1301 and also between outlet end 1303 and the trap to detect the size and number for particles exiting the packed bed column, which may also be used to detect saturation of the bed and breakthrough of nonvolatile organic molecules from the column bed.

Sample capture element 1301 may comprise a packed bed column to selectively captures breath aerosol non-volatile particles. Capture element 1301 may be disposed to be in fluid communication with system 1313 (FIG. 1B) through port 1314, which may comprise a quick connect/disconnect coupling. A portion of exhaled air drawn through capture element 1301 using pump 1308 may be routed to reservoir 1312 which is fluidly connected with $CO_2$ sensor 1311. Reservoir 1312 may be a well-sealed container and is used to prevent any air leaks from the $CO_2$ sensor. System 1313 may comprise a user interface and an on-off switch to initiate and stop sampling of exhaled breath using element 1301. Additionally, components such as flow controllers, and flow restrictors 1309 may also be packaged in portable subsystem 1313. Subsystem 1304 may comprise a diaphragm pump, such as a mini diaphragm pump 1308. Portable system 1313 may be 11 in.×7.5 in.×5.5 in. (L×D×H) and may include noise cancelling materials such as foam pads to reduce the noise level caused by the pump to less than 45 dB. System 1313 may be disposed at a distance from the sample capture element, for example, outside an intensive care unit in a hospital.

The exemplary packed bed column in capture element 1301 may comprise Hamilton PRP-C18 resin beads as supplied by Sigma Aldrich and other vendors. The bed may be held in place between two porous filter plates such as frit discs. For example, a polyethylene disc having an average pore size of above 35 μm may be placed upstream of the bed and a polyethylene disc having an average pore size of 10 μm (Boca Scientific, Dedham, MA) may be placed downstream of the bed. The 35 μm frit disc allows a faster air flow rate while the smaller 10 μm frit disc traps all the C18 resin well. In an exemplary element 1301, the packed bed may comprise about 25 mg of C18 resin beads having a nominal diameter between about 12 μm and about 20 μm. Non-volatile organic components in exhaled breath removably interact with the C18 functional groups on the beads and are trapped. Water, volatiles and other hydrophilic molecules pass through the bed and may be trapped in glass trap.

Besides C18 functional groups, other functional groups that show affinity to nonvolatile molecules may be used as adsorbents in the column immobilized on solid phase beads such as resin beads. The solid phase beads may be made of polymers and particles such as resins, cellulose, silica, agarose, and hydrated $Fe_3O_4$ nanoparticles. Adsorbent materials may comprise other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also comprise at least one of ion exchange phases, polymer phases, antibodies, glycans, lipids, DNA and RNA. For capturing aerosolized virus particles, exemplary sample capture element 1301 may comprise sulfate ester-immobilized cellulose beads. Alternately, sample capture element 1301 may comprise packed beds of C18 beads and sulfate ester-immobilized cellulose beads. Alternately, sample capture element 1301 may comprise a packed bed of a mixture of C18 beads a sulfate ester-immobilized cellulose beads. Exemplary sulfate beads may comprise Cellufine Sulfate beads (JKC Corp., Japan). Particle diameter may be between about 40 μm and about 130 μm. An exemplary sample capture element may comprise about 100 mg of sulfate ester-immobilized cellulose beads disposed as a packed bed column. The exemplary sample capture element may have an internal diameter of about 7 mm and length of about 30 mm.

The capacity of the C18 beads in element 1301 to capture non-volatile organic molecules may be between about 0.05 mg (non-volatile organics)/mg beads and about 0.5 mg/mg. The capacity of C18-bonded resin beads in the column bed in exemplary capture element may be about 0.1 mg/mg. That is, a column bed having 25 mg C18 beads would be expected to be characterized by a capacity to trap or adsorb about 2.5 mg of non-volatile organic molecules. Pump 1308 may be a diaphragm pump. Data from the $CO_2$ sensor may be recorded on a non-volatile memory card such as an SD card that is commonly used in portable devices. A flow rate sensor may be installed to monitor the flow rate through the C18 packed bed column. Alternately, a flow controller may be employed to achieve a consistent flow rate, for example, a flow rate of 500 mL/min through the packed bed column. To enable exhaled breath aerosol sampling from a ventilator disposed in hospital intensive care units using exemplary capture element 1301, pump 1308 may be packaged along with a $CO_2$ sensor 1311, associated power supply 1307, system control components, and required fluidic components (tubings, quick connect/disconnect couplings at the like) into a portable system 1313 (FIG. 1B).

Disclosed is an exemplary diagnosis system 2000 (FIG. 2), which may comprise a breath sample collection system 2001 disposed in fluid communication with a sample extraction system 2002 and an analysis system 2003. The sample collection system 2001 may comprise exemplary collection system 1301 as described above. After a predetermined sample collection period, sample capture element 1301 may be removed from system 1300. Element 1301 may then be autoclaved at 110° C. for about 10 minutes to disinfect element 1301 prior to extracting the captured aerosol particles. Captured non-volatile aerosol particles may be extracted by washing (or flushing) the column with about 200 μL to about 400 μL of a solvent comprising at least one of 70% acetonitrile (ACN), about 50% to about 70% methanol, and about 50% to about 70% isopropyl alcohol (IPA). For example, 50% ACN flush may be used to elute metabolites and proteins in a first-stage flush followed by 70% IPA flush to elute lipids from the packed bed column. The organic solvent may be removed, if needed, from the packed bed column by lyophilization overnight to preserve the captured bioaerosol particles. The organic solvent may be also removed by incubating on a heating block at about 70° C. for about 30 minutes. Finally, the bed may be washed with about 0.05% TFA (trifluroacetic acid). The sample extraction system may be used to extract the trapped non-volatile organics from the packed bed column in system 1300 and may be disposed in-line or off-line in system. When system 2002 is disposed off-line, at the conclusion of exhaled breath sample collection, capture element 1301 may be removed from system 1300 and eluted with an organic solvent in extraction system 2002 to remove non-volatile organics from the packed bed column. Exemplary organic solvents include, but are not limited to, about 50-70% acetonitrile in water to extract trapped non-volatile organics (strongly polar non-volatile organic molecules, proteins and the like) from the packed bed column. The extraction may be repeated using the same or another solvent, that includes, but is not limited to 50-70% isopropanol in water to extract less polar lipid molecules from the packed bed. Other organic solvents include between about 50% and about 70% methanol in water, and about 50% methanol in about 50% chloroform. When system 2002 is disposed in-line, at least one of a $CO_2$ sensor and particle counter may be disposed upstream of extraction system 2002. System 2002 may comprise a solvent vessel, a pump to transfer the solvent from the solvent to packed bed column, and a vessel to collect the solvent comprising the non-volatile biomarkers into another vessel or cup. Alternately, system 2002 may comprise an injector to inject solvent into the packed bed column and collect the extract liquid comprising non-volatile organics and biomarkers in a suitable cup or vessel, or other laboratory tubes having a small volume. The captured sample in solvent may be further processed and analyzed in analysis system 2003.

Many diagnostic devices may be adapted for use in analysis system 2003 that include, but are not limited to, devices that perform genomics-based assays (such as PCR, rt-PCR and whole genome sequencing), biomarker recognition assays (such as ELISA), and spectral analysis such as mass spectrometry (MS). Of these diagnostic devices, MS is preferable on account of its speed of analysis. The MS techniques that are preferable for biomarker identification are electrospray ionization (ESI) and matrix assisted laser desorption ionization (MALDI) time of flight MS (TOFMS). ESI may be coupled to high resolution mass spectrometers. MALDI-TOFMS devices may be compact, lightweight, consume less than 100 watts of power and provide sample analysis in less than 15 minutes. MALDI-TOFMS is a preferred diagnostic device for point-of-care diagnostics suitable for ACF. The sample must be dry before it is inserted into the vacuum chamber of the MS and subjected to laser pulses from an ultraviolet laser. This interaction between the sample and the laser creates large, informative biological ion clusters that are characteristic of the biological material. When a concentrated sample is provided by sample processing system 2004 comprising only trace levels of water or trace levels organic solvents such as 50% to 70% of one of acetonitrile, methanol, and isopropanol in water, sample analysis using MS may take less than 5 minutes (including the sample preparation) because less time is needed to evaporate the water from the sample.

MALDI-TOFMS may be used to identify live/active agents that include, but are not limited to, *B. anthracis* spores (multiple strains), *Y. pestis, F. tularensis*, Venezuelan equine encephalitis virus (VEE), Western equine encephalomyelitis virus (WEE), Eastern equine encephalitis virus (EEE), botulinum neurotoxins (BoNT), *staphylococcus* Enterotoxin (SEA), Staphylococcal enterotoxin B (SEB), ricin, abrin, Ebola Zaire strain, aflatoxins, saxitoxin, conotoxins, Enterobacteria phage T2 (T2), HT-2 toxins (HT2), cobra toxin, biothreat simulants including *B. globigii* spores, *B. cereus* spores, *B. thuringiensis* Al Hakam spores, *B. anthracis* Sterne spores, *Y. enterocolitica, E. coli*, MS2 virus, T2 virus, Adenovirus and nonvolatile biochemical threats including NGAs (nonvolatile), bradykinin, oxytocin, Substance P, angiotensin, diazepam, cocaine, heroin, and fentanyl. Further, the exemplary systems and methods disclosed herein may be used to achieve accurate detection and identification of SARS-CoV-2 from human breath samples.

In "matrix assisted laser desorption ionization" (MALDI), the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field. Microbiology and proteomics have become major application areas for mass spectrometry; examples include the identification of bacteria, discovering chemical structures, and deriving protein functions. MALDI-MS has also been used for lipid profiling of algae. During MALDI-MS, a liquid, usually comprised of an acid, such as trifluoroacetic acid (TFA), and a MALDI matrix chemical such as alpha-cyano-4-hydroxycinnamic acid, is dissolved in a solvent and added to the sample. Solvents include acetonitrile, water, ethanol, and acetone. TFA is normally added to suppress the influence of salt impurities on the mass spectrum of the sample. Water enables hydrophilic proteins to dissolve, and acetonitrile enables the hydrophobic proteins to dissolve. The MALDI matrix solution is spotted on to the sample on a MALDI plate to yield a uniform homogenous layer of MALDI matrix material on the sample. The solvents vaporize, leaving only the recrystallized matrix with the sample spread through the matrix crystals. The acid partially degrades the cell membrane of the sample making the proteins available for ionization and analysis in an MS. Other MALDI matrix materials include 3,5-dimethoxy-4-hydroxycinnamic acid (sinapinic acid), α-cyano-4-hydroxycinnamic acid (α-cyano or α-matrix) and 2,5-dihydroxybenzoic acid (DHB) as described in U.S. Pat. No. 8,409,870.

The analytical methods for the analysis of metabolites, proteins, and lipids may include silver staining for protein profiling, protein assay for protein content, bottom-up proteomics and LC-MS/MS for metabolomics and lipid-omics, and MALDI-TOF mass spectrometry for molecule profiling. In an exemplary test, exhaled breath aerosol from patients infected with pneumonia were collected using capture element 1301 connected to a ventilator. During subsequent analysis, protein content measured using protein assay and molecule profiling measured using MALDI-TOF MS were found to be good indicators of pneumonia infection in patients as revealed by Pearson's correlation heatmap comprising the variables of collected total exhaled air volume, $CO_2$ content in exhaled air, protein content, MALDI-TOF total ion intensity and MALDI-TOF MS single peak (4820 m/z) intensity.

Analysis system 2003 may comprise sample processing system 2004 and at least one diagnostic device 2005. Sample processing system 2004 may comprise elements necessary to perform one or more of the following steps:

(a) Placing the sample in at least one of a cup, a vial and a sample plate. For example, the Series 110A Spot Sampler (Aerosol Devices) uses 32 well plates with circular well shape (75 μL well volume) or teardrop well shape (120 μL well volume) which are heated to evaporate the solvent and excess fluid/liquid in the sample to concentrate the sample;

(b) Placing the sample in a cup and exposed to a source of vacuum or freeze-drying device to cause the solvent to evaporate to concentrate the sample; and, (c) hot digestion of proteins and virus particles The samples may be centrifuged to remove chemical contamination particles.

Virus (e.g., SARS-CoV-2) detection is centered on detection of viral proteins, which is a difficult challenge. An exemplary method for virus detection may comprise glycan-based capture matrix (beads) to pull the target virus out of the background matrix (e.g., other non-virus biomolecule, contaminants). An aliquot of the sample collected using sample collection system 1300 may comprise other background contaminants and may be applied to a bead carrying the capture probe. At least one of glycan, heparin, and carbohydrates may be used as capture materials or probes bound on resin beads or similar types of beads. An optional washing step may be used to remove any nontargeted-virus contaminants. The concentrated and purified virus may be eluted off the beads using suitable solvents into a sealed heating chamber containing an organic acid which may comprise formic acid or acetic acid and heated to 120° C. for about 10 minutes to digest the proteinaceous toxin down into specific peptide fragments. This hot acid protein digestion protocol cleaves the protein at aspartic acid residues creating a highly reproducible peptide pattern. The capture and digestion processes described may be accomplished with antibodies and enzyme, respectively. Using this exemplary sample processing for MALDI-TOFMS, sensitivity for ricin biotoxin of better than 100 ng/mL (with S/N of about 50:1) in clean buffer was achieved. At S/N (signal to noise ratio) of 3:1, limits of detection (LOD) of <10 ng/mL may be achieved. For the 1 μL samples used in the MALDI-TOFMS analytical systems, about 10 ng/mL LOD equates to a total mass of about 10 pg ($10^{-12}$ g) on the probe, which is equivalent to about 20,000 viral particles. An exemplary microfluidic sample processing system to implement the method disclosed above may be configured to analyze samples collected from the air or from other sources such as nasal swabs. The glycan-based capture column and other microfluidics components may be reusable. Large fluid reservoirs containing buffer, weak acids, and alcohols may be employed to provide sufficient capacity to measure 100's of samples in one channel of the system. Multiple systems may be run in parallel to process multiple samples simultaneously. Since no fragile and expensive biomolecular reagents are required, the system is cost effective.

Hot acid digestion cleaves the proteins reproducibly at aspartic acid residues creating known peptide sequences with known masses. These peptide mass distributions are characteristic of the progenitor proteins. Thus, digestion provides outstanding specificity if the proteins of interest are largely separated from background materials. Furthermore, the peptide mass distribution is directly determined by the genome, accounting for post-translational modifications. As soon as a new virus is isolated, it is rapidly sequenced. The RNA sequence of the SARS-CoV-2 virus may be used to accurately predict the protein sequences with modern bioinformatics tools (ExPASy bioinformatics portal). These proteins can then be "digested" in silico using bioinformatics tools to create a theoretical peptide map. Thus, the peptides that arise from SARS-COV-2 digestion can be predicted and compared to experimental data to generate a specific MALDI TOFMS signature of the organism. Reports suggest that the predominant proteins in SARS-CoV are characterized by about 46 kDa nucleocapsid protein and the 139 kDa spike proteins. Other proteins in reasonable abundance are E, M and N proteins.

Detection specificity of a target virus will require some level of background removal, particularly if the background contains other proteins. If large amounts of exogenous proteins are present, the peptide map could be dominated by non-target peptides. As previously described, affinity capture probes for the virus toxins based on glycan-decorated agarose beads may be used to readily clean up the toxins, even in large excess of background proteins, and other biomolecules. When analyzing exhaled breath for virus targets such as SARS-CoV-2, other human proteins in breath may interfere with detection specificity. An affinity-based cleanup of the sample is required to ensure highest specificity. Virus detection may require bead materials that provide more selective affinity compared to the glycan-decorated beads previously described. For example, dextran-based adsorbents may be used for purifying viruses, including coronaviruses, but the affinity of this resin for the target virus may not be satisfactory. As an alternative, carbohydrates may be used for viral and protein purification including target viruses such as SARS-CoV and SARS-CoV-2. Further heparin, and heparan sulfate may be used as binding agents bound to resin beads. Heparin covalently linked to sepharose beads (GE Healthcare Life Sciences, Heparin Sepharose 6 Fast Flow affinity resin Product #17099801) may be used instead of glycan capture beads. This resin may enable bead-based capture affinity capture system for collecting virus particles from exhaled breath. In an exemplary diagnostic system, exhaled breath samples may be pulled through a capture bed in a sample collection system 1300, collecting particles from the breath of patient. The resin beads (bed) may be washed to remove any background material. The viral particles adsorbed to the beads would then be eluted off using high concentration of acid solution, such as at least one of about 12.5% acetic acid, about 5% TFA, about 5% formic acid and about 10% HCl, into the hot acid digestion chamber to generate the characteristic peptides. The peptide samples may be mixed with MALDI matrix and deposited onto as suitable substrate for MALDI TOFMS analysis. The samples may also be deposited on a suitable substrate or disk that is precoated with MALDI matrix.

Reports suggests that analysis of nose and throat swabs from influenza patients and COVID-19 patients produce viral counts of between about $10^3$ and $10^{10}$ viral particles. Less is known about the viral particles count in the breath of patients. Other reports suggest that influenza patients exhaled >$10^4$ particles in about 30 minutes of breathing. If the output of SARS-CoV-2 is similar to that of influenza, an output of $10^3$ to $10^4$ particles in exhaled breath with a particle collection efficiency of >99.9% should be sufficient to identify the target virus particles in exhaled breath using the exemplary methods and systems disclosed herein. Detection time using the exemplary systems and methods may be between about 10 minutes and 20 minutes include the steps of sample extraction (breathing maneuvers), sample collection, sample processing (digestion) and analysis using a MALDI TOF-MS. This detection time is quite rapid compared to existing detection systems.

An exemplary sample processing component may comprise a hot acid digestion module or cartridge to autonomously extract sample from the packed bed column 1301, perform sample clean-up, conduct the hot acid digestion and provide a sample ready for plating on a MALDI-TOFS sample substrate or disk. The cartridge may be designed for reusability by adding the capability to flush the cartridge between uses.

In the exemplary systems and methods described herein, the packed bed column length (L) in sample capture element 1301 is about 3 mm. The nominal internal diameter of the tube is about 7 mm (D). An exemplary packed bed comprising about 25 mg of C18 resin beads having a nominal particle diameter ($D_p$) of between about 12 μm and 20 μm, yields a $L/D_p$ ratio of between about 150 and 250 at a $D/D_p$ ratio of about 350 to about 580. These column parameters were found to prevent undesirable localized flow distributions in the bed to ensure that substantially all resin beads were exposed to the aerosol flow through the bed.

The disclosed exemplary systems and methods may be used to establish a baseline of protein, metabolite, and lipids signatures in exhaled breath, which may then be used during to differentiate between the exhaled breath of patients with various diseases and offer a powerful diagnostic tool for disease detection based on the analysis of non-volatile aerosols in exhaled breath.

The disclosed exemplary systems and methods may also be used for detection, monitoring and treatment of diseases other than respiratory diseases and infectious diseases. Chen et al. (2019) describe a top-down proteomic strategy for the global identification of truncated proteins without the use of chemical derivatization, enzymatic manipulation, immunoprecipitation, or other enrichment. More than 1000 truncated proteoforms were identified. Tsai et al. (2022) describe mass spectrometry based diagnostic detection of the novel coronavirus infectious disease (COVID-19) as a useful alternative to classical PCR based diagnostics. Nanoscale liquid chromatography tandem MS was used to identify endogenous peptides found in nasal swab saline transport media to identify endogenous peptides and endogenous protease cut sites. They report that SARS-CoV-2 viral peptides were not readily detected and are highly unlikely to be responsible for the accuracy of MALDI based SARS-CoV-2 diagnostics. Lipton et al. (2018) evaluated the association of specific collagen fragments measured in serum in two independent metastatic breast cancer cohorts and report that collagen fragments quantified in pretreatment serum was associated with shorter time-to-progression and overall survival in the two independent cohorts receiving systemic therapy. Ahmed et al. (2005) measured protein glycation, oxidation and nitration adducts released by cellular proteolysis using LC-MS/MS to quantify increased protein damage and flux of proteolytic degradation products in blood and urine samples of Type 1 diabetic patients. Parchi et al. (1998) examined genomic DNA isolated from frozen tissue from the cerebral cortex, basal ganglia, and cerebellum of patients using SDS-Page electrophoresis and MALDI TOFMS and found that different patterns of truncated prion protein fragments correlated with distinct phenotypes in P102L Gerstmann-Sträussler-Scheinker disease.

EXAMPLES

Example 1. Capture and Analysis of Exhaled Air Aerosols of Patients Diagnosed with COVID-19 Using an Exemplary Packed Bed Column Connected to a Ventilator Exemplary system 1300 (FIG. 1A) was evaluated in a hospital intensive care unit (ICU) dedicated for treating patients diagnosed with the COVID-19 disease. The flow rate through the packed bed column comprising about 25 mg of C18 beads (20 μm nominal diameter) in sample capture element 1301 was set at 500 ml/min. Before installing in system 1300, the capture element was washed with 70% acetonitrile once and then thrice with 0.05% TFA. The capture elements were stored at 4° C. before use to prevent drying out of the C18 beads in the packed bed. Exhaled breath aerosol was then collected for about 4 h from each patient at a flow rate of 500 ml/min. After the collection period, the packed bed columns were removed from the collection system. The columns were washed with about 200 μL to about 400 μL of 70% ACN or 70% IPA. The organic solvent was removed from the packed bed column by lyophilization overnight. The organic solvent may also be removed by placing element 1301 on a heating block at about 70° C. for about 30 minutes. The captured aerosol particles were extracted or resolved using between about 40 μL and 100 μL of 0.05% TFA. The samples were then analyzed using SDS-PAGE electrophoresis and silver staining, MALDI-TOFMS (whole cell top-down proteomics), and bottom-up proteomics.

About 5 μl of total collected sample was used for SDS-PAGE electrophoresis, which was conducted using a Criterion Tris-HCl Gel system (Bio-Rad Laboratories, Hercules, CA). After SDS-PAGE electrophoresis, the SDS-PAGE gel was prepared with a silver staining kit (Thermo Fisher Scientific) for the visualization of protein bands. Bovine serum albumin was used as an internal positive control. Protein bands were observed in all 3 patient samples. Based on the BSA control sample, the protein content in 3 samples was estimated to be at least 100 ng.

For whole cell MALDI-TOFMS analysis, 0.2 μL of analytes was mixed with 0.2 μL of α-Cyano-4-hydroxycinnamic acid MALDI matrix (CHCA) prepared in 70% ACN. The mixture was deposited onto a MALDI sample cap and mass spectra were collected using an exemplary MALDI-TOF mass spectrometry system disclosed in commonly owned Pat. Appl. No. PCT/US20/48042 titled "SYSTEMS AND METHODS OF RAPID AND AUTONOMOUS DETECTION OF AEROSOL PARTICLES," which is incorporated by reference herein in its entirety. MALDI-TOF spectra were collected from the samples of patient #3 and #4. Mass peaks were observed in both samples. The peak patterns generated from MALDI-TOF MS were examined using pattern recognition algorithms for detection and classification.

For bottom-up proteomics, 5 μl of each sample was used. About 50 μl of 50 mM ammonia bicarbonate (pH 8.5) was added to each sample. Protein reduction was conducted by adding dithiothreitol to a final concentration of 5 mM and incubating for 30 min at 37° C. After reduction, protein alkylation was followed by adding iodoacetamide to a final concentration of 15 mM and incubating for 1 h at room temperature. Trypsin (Thermo Fisher Scientific) was used for an overnight protein digestion. After digestion, peptides were cleaned up using C18-packed tips (Glygen, Columbia, MD). The peptide samples in 20 μl of 0.1% formic acid were then prepared for mass spectrometry analysis, including MALDI-TOF mass spectrometry. Samples were processed using an EASY-nLC 1000 system (Thermo Fisher Scientific) coupled to a LTQ Quadrupole-Orbitrap mass spectrometer (Thermo Fisher Scientific). For tandem mass spectrometry analysis, peptides were loaded into an Acclaim PepMap 100 C18 trap column (0.2 mm×20 mm, Thermo Fisher Scientific) with a flow rate of 5 μl/min and separated on an EASY-Spray HPLC Column (75 μm×150 mm, Thermo Fisher Scientific). HPLC gradient was conducted using 5%-55% of the mobile phase (75% acetonitrile and 0.1% formic acid) with a flow rate of 300 nl/min for 60 min. Mass spectrometry data collection was conducted in the data dependent acquisition mode. Precursor scanning resolution was set to 30,000 and product ion scanning resolution 15,000. Product ion fragmentation was achieved using high energy collision-induced disassociation with 30% total energy. The bottom-up proteomics raw data files were processed with MaxQuant Andromeda software (maxquant.org) against the "human" and "SARS-COV-2" protein database (uniprot.org) following the standard recommendations and instructions. Human protein database included 20,395 reviewed proteins and SARS-COV-2 protein database included 13 reviewed proteins. Liquid chromatography profiles and peptide fingerprints generated from the digested peptides were identified using LC-MS and MALDI-TOF MS in all three patient samples. In total, 222 proteins identified in all three patient samples. Most proteins were found to originate from human blood, indicating active interaction between lungs and blood. As shown in Table 1, typical lung proteins and SARS-COV-2 protein were identified.

umns were then eluted with about 300 μL of 70% isopropyl alcohol (IPA) to extract proteins and peptides. The solvent was then removed by an overnight lyophilization. After

TABLE 1

Proteins identified from exhaled air aerosols collected from patients diagnosed with COVID-19.

| Protein identification list | Mol. weight [kDa] |
| --- | --- |
| sp\|P0DTD1\|R1AB_SAR52 Replicase polyprotein 1ab OS = Severe acute respiratory syndrome coronavirus 2 OX = 2697049 GN = rep PE = 1 SV = 1 | 794.05 |
| sp\|Q9HC84\|MUC5B_HUMAN Mucin-5B OS = Homo sapiens OX = 9606 GN = MUC5B PE = 1 SV = 3 | 596.33 |
| sp\|P02671\|FIBA_HUMAN Fibrinogen alpha chain OS = Homo sapiens OX = 9606 GN = FGA PE = 1 SV = 2 | 94.972 |
| sp\|P02768\|ALBU_HUMAN Serum albumin OS = Homo sapiens OX = 9606 GN = ALB PE = 1 SV = 2; | 69.366 |
| sp\|P02675\|FIBB_HUMAN Fibrinogen beta chain OS = Homo sapiens OX = 9606 GN = FGB PE = 1 SV = 2 | 55.928 |
| sp\|Q8TDL5\|BPIB1_HUMAN BPI fold-containing family B member 1 OS = Homo sapiens OX = 9606 GN = BP1FB1 PE = 1 SV = 1 | 52.441 |
| sp\|P63261\|ACTG_HUMAN Actin, cytoplasmic 2 OS = Homo sapiens OX = 9606 GN = ACTG1 PE = 1 SV = 1; sp\|P60709\|ACTB_HUMAN Actin, cytoplasmic 1 OS = Homo sapiens OX = 9606 GN = ACTB PE = 1 SV = 1 | 41.792 |
| sp\|P35247\|SFTPD_HUMAN Pulmonary surfactant-associated protein D OS = Homo sapiens OX = 9606 GN = SFTPD PE = 1 SV = 3 | 37.728 |
| sp\|P02647\|APOA1_HUMAN Apolipoprotein A-1 OS = Homo sapiens OX = 9606 GN = APOA1 PE = 1 SV = 1 | 30.777 |
| sp\|Q8IWL2\|SFTA1_HUMAN Pulmonary surfactant-associated protein A1 OS = Homo sapiens OX = 9606 GN = SFTPA1 PE = 1 SV = 2; sp\|Q8IWL1\|SFPA2_HUMAN Pulmonary surfactant-associated protein A2 OS = Homo sapiens OX = 9606 GN = SFTPA2 PE = 1 SV = 1 | 26.242 |
| sp\|P68871\|HBB_HUMAN Hemoglobin subunit beta OS = Homo sapiens OX = 9606 GN = HBB PE = 1 SV = 2 | 15.998 |
| sp\|P69905\|HBA_HUMAN Hemoglobin subunit alpha OS = Homo sapiens OX = 9606 GN = HBA1 PE = 1 SV = 2 | 15.257 |
| sp\|Q99879\|H2B1M_HUMAN Histone H2B type 1-M OS = Homo sapiens OX = 9606 GN = H2BC14 PE = 1 SV = 3; sp\|Q99877\|H2B1N_HUMAN Histone H2B type 1-N OS = Homo sapiens OX = 9606 GN = H2BC15 PE = 1 SV = 3; sp\|Q93079\|H2B1H_HUMAN Histone H2B type 1-H OS = Homo sapiens OX = 9606 GN = HIST1H2BH PE | 13.989 |
| sp\|P0DJI8\|SAA1_HUMAN Serum amyloid A-1 protein OS = Homo sapiens OX = 9606 GN = SAA1 PE = 1 SV = 1 | 13.532 |
| sp\|P06702\|S10A9_HUMAN Protein S100-A9 OS = Homo sapiens OX = 9606 GN = S100A9 PE = 1 SV = 1 | 13.242 |
| sp\|P02656\|APOC3_HUMAN Apolipoprotein C-III OS = Homo sapiens OX = 9606 GN = APOC3 PE = 1 SV = 1 | 10.852 |
| sp\|P11684\|UTER_HUMAN Uteroglobin OS = Homo sapiens OX = 9606 GN = SCG81A1 PE = 1 SV = 1 | 9.9937 |

Example 2. Collection of Exhaled Aerosol Samples from Intubated Patients with Respiratory Tract Infection and Analysis of Captured Truncated Proteoforms in Exhaled Breath Using Top Down Proteomics Positive microorganism culture using tract specimens, including sputum, nasal swab, bronchoalveolar lavage (BAL), and endotracheal tube liquid, was used to first diagnose respiratory tract infection (RTI) in intubated patients. Based on the culture results, 25 exhaled aerosol samples were collected from intubated patients with RTI using exemplary system 1300, and 22 exhaled aerosol samples were collected from intubated patients without RTI (non-RTI). Sample capture element comprised C18 resin beads having a nominal diameter of between about 12 μm and about 20 μm. The packed bed was washed once with 300 μL of 70% IPA and 300 μL of water before installing in system 1300. The resin beads were packed between two porous polymeric frit discs. The internal diameter of the sample capture element was about 7 mm. The length of the packed bed column was about 3 mm. One capture element was used for each aerosol sample. After sample collection, the columns were disinfected (decontaminated). The collyophilization, about 50 μL of 0.05% TFA was added to each sample for LC-MS/MS analysis.

For LC-MS analysis, about 18 μL of each sample was injected into a microflow C18 column (Acclaim™ Pep-Map™ 100, 75 μm×2 μm×250 mm, Thermo Fisher Scientific) and proteins were separated using a gradient of solvent (80% acetonitrile with 0.1% formic acid) from 5% to 70% in 60 minutes using an EASY-nLC 1000 system (Thermo Fisher Scientific). Ion fragmentation was conducted using collision-induced dissociation (CID, 35% collision energy). Raw mass spectrometry data files were searched against Human Swiss-Prot protein database containing 20377 reviewed entries, and truncated proteoforms were identified using MaxQuant software (Max-Planck-Institute of Biochemistry). Intensity values (arbitrary units generated in the mass spectrometer) of each identified proteoform were extracted from MaxQuant searching results. Each sample was first normalized by using total intensity values. Missing values (zero values) were replaced by 1000, which is two magnitudes lower than the lowest intensity value observed in the samples. Subsequently, the values were transformed with the logarithm with base 10. For example, a value of 10000 will be 5 after data transformation. Two-tailed unpaired t-test was applied to RTI and non-RTI groups, and the raw p values were adjusted using Benjamini-Hochberg method with the 0.05 false-discovery rate (FDR). Receiver operating characteristic (ROC) curves were constructed and area under the ROC curve (AUC) was calculated using each feature with statistical significance between the RTI and non-RTI groups and a generalized linear model created by a binomial logistic regression of all significant features. The ROC curve is plotted with TPR (true positive rate) against the FPR (false positive rate) where TPR is on the y-axis and FPR is on the x-axis.

Figure 3D:
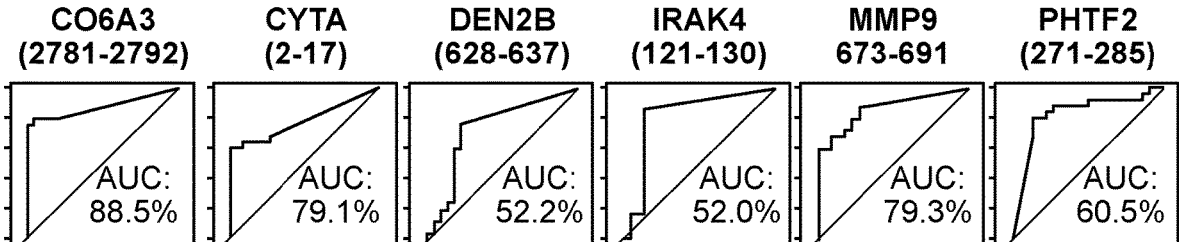
Figure 3E:
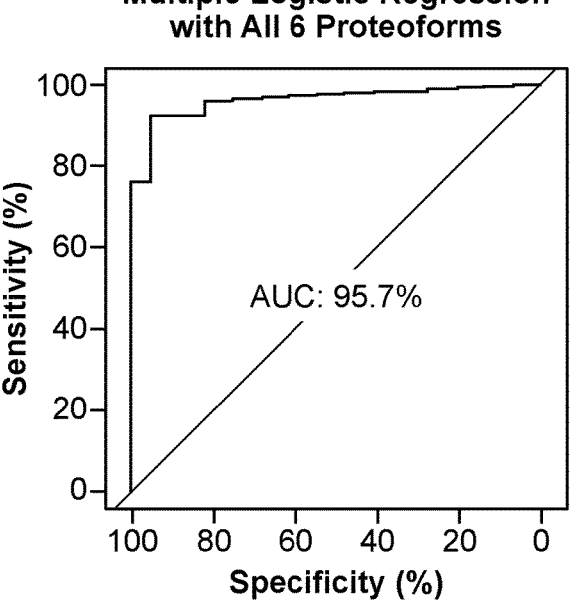

263 truncated proteoforms of 80 proteins were identified (Table 2). Further, the number of truncated proteoforms identified in the exhaled aerosol samples of RTI patients was higher than that of the samples from non-RTI intubated patients. (FIG. 3A). In the Box and Whisker plot (FIG. 3A), the boxes indicate quartiles, and the horizontal lines within each box is indicative of the median count in each case. The whiskers related to each "box" indicate the maximum and minimum of each range. The mean count in each case is indicated with a cross mark.

constructed to include the 6 truncated proteoforms as predictors by using glm( ) function in RStudio. RStudio is an integrated development environment for the programming language R for statistical computing and graphics. GLM in R is a class of regression models that supports non-normal distributions and can be implemented in R through glm( ) function that takes various parameters, and allows the user to apply various regression models. The AUC is calculated based on the logistic regression model. The AUC values suggest that each individual truncated proteoform may not be useful in distinguishing between RTI and non-RTI patients; that is, they may not be useful in class separation between RTI and non-RTI patients. A linear regression model was constructed using multiple logistic regression with all six truncated proteoforms, and the AUC was found to be 95.7% (FIG. 3E). This high AUC value suggests that these six truncated proteoforms, when taken together, may be used as the basis for distinguishing between patients with RTI and those without RTI. An excellent model has AUC of about 1 which indicates good separability between RTI and non-RTI patients.

TABLE 2

Protein list related to truncated proteoforms from
analysis of the samples collected from intubated patients.
Protein ID, Swiss-Prot

| | | | | | | | |
|---|---|---|---|---|---|---|---|
| A4D0S4 | O95744 | P11021 | P35908 | P68870 | Q643R3 | Q96F81 | Q9NWZ3 |
| A4FU69 | P00441 | P11684 | P40121 | P68871 | Q7Z5P9 | Q96M83 | Q9NXW2 |
| A5PLN9 | P01040 | P12111 | P47874 | P69905 | Q86UP3 | Q96ME1 | Q9NZ32 |
| A8MX34 | P01834 | P12814 | P49619 | P78524 | Q8IV20 | Q96QF7 | Q9NZI4 |
| O14523 | P01876 | P13645 | P50748 | Q02413 | Q8N394 | Q99985 | Q9UHL4 |
| O14640 | P02749 | P14780 | P54198 | Q02447 | Q8N3S3 | Q9C005 | Q9UKT7 |
| O14950 | P02768 | P21333 | P59665 | Q13535 | Q8NBR0 | Q9C0A1 | Q9ULT0 |
| O75494 | P04083 | P22894 | P60660-2 | Q14692 | Q8TDL5 | Q9C0D6 | Q9Y2F5 |
| O75594 | P04264 | P24158 | P61626 | Q2M2D7 | Q92608 | Q9H799 | Q9Y5X3 |
| O95069 | P06702 | P35527 | P63261 | Q53RT3 | Q93038 | Q9H8H0 | Q9Y6S9 |

Further, volcano plots extracted from the t-test showed that the ion intensity of six truncated proteoforms were significantly higher in RTI samples than in non-RTI samples (FIG. 3B). The distribution of the 6 truncated proteoforms are shown in FIG. 3C and Table 3. As shown in FIG. 3C, the ion intensity of each proteoform in samples of RTI patients was significantly higher than that of non-RTI patients, with the exception of the proteoform corresponding to protein PHTF2.

The disclosed exemplary methods and systems may also be used to capture truncated proteoforms in exhaled breath collected using masks worn by patients in an out-patient setting and from ambient air for active case finding or other diagnostic purposes as disclosed in commonly owned International Appl. No. PCT/US22/22964, which is incorporated by reference herein in its entirety.

The Abstract is provided to comply with 37 C.F.R. § 1.72(b), to allow the reader to determine quickly from a

TABLE 3

Listing of six truncated proteoforms with intensities higher
in samples from RTI patients than from non-RTI patients.

| Proteoforms | Protein Name | Protein ID | Position Amino Acid | Fold Change, [log2] RTI/nonRTI | p, [−log10] FDR 0.05 |
|---|---|---|---|---|---|
| KEVYTFASEPND | CO6A3 | P12111 | 2781-2792 | 0.87 | 7.13 |
| FCQDRFYWRVSSRSELNQV | MMP9 | P14780 | 673-691 | 0.74 | 6.08 |
| TETDNGYVSLDGKKT | PHTF2 | Q8N3S3 | 271-285 | −0.71 | 4.99 |
| QQKQMPFCDK | IRAK4 | Q9NWZ3 | 121-130 | 0.65 | 4.58 |
| IPGGLSEAKPATPEIQ | CYTA | P01040 | 2-17 | 0.61 | 3.51 |
| RGKKRLKKLS | DEN2B | P78524 | 628-637 | 0.45 | 3.44 |

These six proteoforms are characteristic of respiratory tract infections (such as pneumonia, empyema) caused by a variety of bacteria and fungi, including *Pseudomonas aeruginosa, Klebsiella pneumonia, Citrobacter koseri*, and methicillin resistant (MRSA) *Staphylococcus aureus*. ROC curves were constructed using each truncated proteoform and AUC was calculated for the classification of RTI and non-RTI samples (FIG. 3D). A logistic regression model was cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. N. Ahmed, R. Babaei-Jadidi, S. K. Howell, P. J. Beisswenger & P. J. Thornalley, "Degradation products of proteins damaged by glycation, oxidation and nitration in clinical type 1 diabetes," *Diabetologia* 48, 1590-1603 (2005).
2. Dapeng Chen, Lucia Geis-Asteggiante, Fabio P. Gomes, Suzanne Ostrand-Rosenberg, and Catherine Fenselau, "Top-Down Proteomic Characterization of Truncated Proteoforms," *J. Proteome Res.* 2019, 18, 11, 4013-4019.
3. Hunt, J., "Exhaled breath condensate: An evolving tool for noninvasive evaluation of lung disease," *J Allergy Clin. Immunol.* 2002; 110:28-34.
4. Allan Lipton, Kim Leitzel, Suhail M. Ali, Hyma V. Polimera, Vinod Nagabhairu, Eric Marks, Angelique E. Richardson, Laura Krecko, Ayesha Ali, Wolfgang Koestler, Francisco J. Esteva, Diana J. Leeming, Morten A. Karsdal, Nicholas Willumsen, "High turnover of extracellular matrix reflected by specific protein fragments measured in serum is associated with poor outcomes in two metastatic breast cancer cohorts," *Intl. J Cancer,* 2018, 43 (11), 3027-3034.
5. Piero Parchi, Shu G. Chen, Paul Brown, Wenquan Zou, Sabina Capellari, Herbert Budka, Johannes Hainfellner, Patricio F. Reyes, Gregory T. Golden, Jean J. Hauw, D. Carleton Gajdusek, and Pierluigi Gambetti, "Different patterns of truncated prion protein fragments correlate with distinct phenotypes in P102L Gerstmann-Sträussler-Scheinker disease," *Neuroscience,* 95 (14), 8322-8327 (1998).
6. Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.
7. Helen Tsai, Brett S. Phinney, Gabriela Grigorean, Michelle R. Salemi, Hooman H. Rashidi, John Pepper, and Nam K. Tran, "Identification of Endogenous Peptides in Nasal Swab Transport Media used in MALDI-TOF-MS Based COVID-19 Screening," *ACS Omega* 2022, 7, 20, 17462-17471.

What is claimed is:

1. An exhaled breath collection system for diagnosis and treatment of a disease, the system comprising:
   one or more sample capture elements comprising a packed bed column in each to selectively capture aerosolized truncated proteoforms characteristic of the disease and present in the exhaled breath produced by a patient; and
   a subsystem comprising one or more of a pump configured to draw the aerosolized truncated proteoforms in the exhaled breath into the one or more sample capture elements, a power supply, or a controller, wherein the subsystem is disposed in fluid communication with the one or more sample capture elements, and is configured to control the operation of the one or more sample capture elements.

2. The system of claim 1, wherein the subsystem further comprises one or more of a $CO_2$ sensor or a particle counter disposed between the one or more sample capture elements and the pump.

3. The system of claim 1, wherein the subsystem is disposed in a portable enclosure.

4. The system of claim 1, wherein the subsystem further comprises a trap disposed between the one or more sample capture elements and the pump and is configured to trap exhaled breath condensate (EBC) comprising one or more of water vapor, volatile organic components, or non-volatile organic components that pass through the one or more sample capture elements.

5. The system of claim 1, wherein each packed bed column comprises solid particles comprising one or more of resins, cellulose, silica, agarose, or hydrated $Fe_3O_4$ nanoparticles.

6. The system of claim 1, wherein each packed bed column comprises one or more of resin beads having C18 functional groups on the surface, cellulose beads having sulfate ester functional groups on the surface, or mixtures thereof.

7. The system of claim 6, wherein the beads have a nominal diameter of at least about 20 μm.

8. The system of claim 6, wherein the beads have a nominal diameter of between about 40 µm and about 150 µm.

9. The system of claim 6, wherein the beads are packed between two porous polymeric frit discs.

10. The system of claim 1, wherein the nominal flow rate drawn through each packed bed column using the pump is between about 200 ml/min and about 3 L/min.

11. The system of claim 1, wherein the subsystem is fluidly and electrically coupled to the one or more sample capture elements using quick connect/disconnect couplings configured to detect mechanical and electrical contact between the subsystem and the one or more sample capture elements and alert a user via a graphical user interface disposed on the subsystem or an audible alarm.

12. A system for diagnosis and treatment of a disease based on capturing truncated proteoforms in exhaled breath, the system comprising:

the exhaled breath collection system of claim 1;

a sample extraction system to extract the captured truncated proteoforms characteristic of the disease from each packed bed column into one or more liquid samples; and an analytical device to analyze the truncated proteoforms in the one more liquid samples.

13. The system of claim 12, wherein the extraction system comprises means to flush each packed bed column with one or more solvents and to collect the one or more solvents comprising truncated proteoforms from each packed bed column.

14. The system of claim 13, wherein the one or more solvents comprises one or more of acetonitrile, methanol, trifluoro acetic acid (TFA), or isopropanol (IPA), the remaining being water.

15. The system of claim 13, wherein the one or more solvents comprise between about 50 vol % and about 70 vol % acetonitrile in water, between about 50 vol % and about 70 vol % isopropanol in water, or about 0.05 vol % TFA in water.

16. The system of claim 12, wherein the analytical device comprises one or more of PCR, ELISA, rt-PCR, mass spectrometer (MS), MALDI-MS, ESI-MS, and MALDI-TOFMS, or LC-MS/MS.

17. The system of claim 1, wherein the truncated proteoforms comprise a class comprising protein CO6A3 (amino acid 2781-2792), CYTA (2-17), DEN2B (628-637), IRAK4 (121-130), MMP9 (673-691), and PHTF2 (271-285).

* * * * *